US010405844B2

(12) United States Patent
Wan

(10) Patent No.: US 10,405,844 B2
(45) Date of Patent: *Sep. 10, 2019

(54) SURGICAL RETRACTOR WITH LIGHT

(71) Applicant: Shaw P. Wan, Norwood, NC (US)

(72) Inventor: Shaw P. Wan, Norwood, NC (US)

( * ) Notice: Subject to any disclaimer, the term of this patent is extended or adjusted under 35 U.S.C. 154(b) by 82 days.

This patent is subject to a terminal disclaimer.

(21) Appl. No.: 15/642,011

(22) Filed: Jul. 5, 2017

(65) Prior Publication Data

US 2017/0296162 A1    Oct. 19, 2017

Related U.S. Application Data

(62) Division of application No. 14/372,484, filed on Jul. 16, 2014, now Pat. No. 9,730,685.

(51) Int. Cl.
| | | |
|---|---|---|
| *A61B 17/00* | (2006.01) | |
| *A61B 17/02* | (2006.01) | |
| *A61B 1/00* | (2006.01) | |
| *A61B 1/06* | (2006.01) | |
| *A61B 1/32* | (2006.01) | |
| *A61B 90/00* | (2016.01) | |
| *A61B 90/30* | (2016.01) | |
| *A61B 17/34* | (2006.01) | |

(52) U.S. Cl.
CPC ........ *A61B 17/0293* (2013.01); *A61B 1/0676* (2013.01); *A61B 1/0684* (2013.01); *A61B 1/32* (2013.01); *A61B 17/02* (2013.01); *A61B 90/36* (2016.02); *A61B 1/00032* (2013.01); *A61B 17/3421* (2013.01); *A61B 2017/00734* (2013.01); *A61B 2090/309* (2016.02); *A61B 2090/3612* (2016.02)

(58) Field of Classification Search
CPC . A61B 17/0293; A61B 17/02; A61B 17/3421; A61B 90/36; A61B 2090/309; A61B 2090/3612; A61B 2017/00734; A61B 1/0676; A61B 1/0684; A61B 1/32; A61B 1/00032
USPC .......................... 600/186–249; 362/255, 612
See application file for complete search history.

(56) References Cited

U.S. PATENT DOCUMENTS

| | | | | |
|---|---|---|---|---|
| 6,497,654 B1 * | 12/2002 | Leonard | ................... | A61B 1/31 600/208 |
| 8,968,186 B2 * | 3/2015 | Tenger | ................. | A61B 1/0684 600/199 |
| 9,730,685 B2 * | 8/2017 | Wan | ......................... | A61B 1/32 |
| 2009/0225159 A1 * | 9/2009 | Schneider | .......... | A61B 1/00124 348/82 |
| 2012/0059226 A1 * | 3/2012 | Funt | ....................... | A61B 17/02 600/213 |

\* cited by examiner

*Primary Examiner* — Pedro Philogene

(74) *Attorney, Agent, or Firm* — Blake E. Vande Garde; Erickson Kernell IP, LLC

(57) ABSTRACT

A surgical retractor has a shaft with an integral blade. The shaft and the blade are joined at an angle. The blade has an upper surface. A plurality of LED lights are embedded within the blade and are exposed at the upper surface. The blade surrounding the LED lights is opaque. The retractor may further include a camera mounted on the blade. Also disclosed is a surgical retractor kit including a mounting ring, at least one of the aforementioned surgical retractors, and a coupler for releasably mounting the retractor to the ring.

19 Claims, 13 Drawing Sheets

SURGICAL RETRACTOR WITH LIGHT

RELATED CASES

This is a divisional application of U.S. patent application Ser. No. 14/372,484 filed on Jul. 16, 2014. The disclosure of that application is expressly incorporated by reference.

FIELD OF THE INVENTION

A surgical retractor with a light is disclosed herein below.

BACKGROUND OF THE INVENTION

Surgical retractors with lights are known. For example, see: U.S. Pat. No. 4,562,832 (Wilder), US Publication No. 2007/0060795 (Vayser), and U.S. Pat. Nos. 7,384,392 & 8,012,089 (both to Bayat). Wilder discloses a retractor with a flexible light pipe. Vayser, in FIG. 1, shows a retractor 1 with a LED (light emitting diode) light 3 and a battery 4. The LED and battery are "all mounted on a strip of tape 8." Vayser, Paragraph 10. Thus, as the invention is described in the independent claims, the lighting components are 'releasably securable' to the retractor. Bayat, on the other hand, shows in FIG. 7, a plurality of LED's 120 along the longitudinal axis of the blade and discloses that the LEDs may be located 'within the profile of the blade.' Bayat '392, column 4, lines 45-58; and Bayat '089, the paragraph bridging columns 5 and 6. Bayat goes on to say that the 'blade near the light is constructed of a translucent or transparent material to allow the light to pass through the blade.' Ibid. Bayat '089 also discloses a camera 136, see FIG. 7, as part of the retractor.

While these retractors are a solution to the problem of providing a light on a retractor, there is room for improvement. The retractor disclosed below is an improvement over these known retractors with a light.

SUMMARY OF THE INVENTION

A surgical retractor has a shaft with an integral blade. The shaft and the blade are joined at an angle. The blade has an upper surface. A plurality of LED lights are embedded within the blade and are exposed at the upper surface. The blade surrounding the LED lights is opaque. The retractor may further include a camera mounted on the blade. Also disclosed is a surgical retractor kit including a mounting ring, at least one of the aforementioned surgical retractors, and a coupler for releasably mounting the retractor to the ring.

DESCRIPTION OF THE DRAWINGS

For the purpose of illustrating the invention, there is shown in the drawings a form that is presently preferred; it being understood, however, that this invention is not limited to the precise arrangements and instrumentalities shown.

DESCRIPTION OF THE INVENTION

Figure 1:
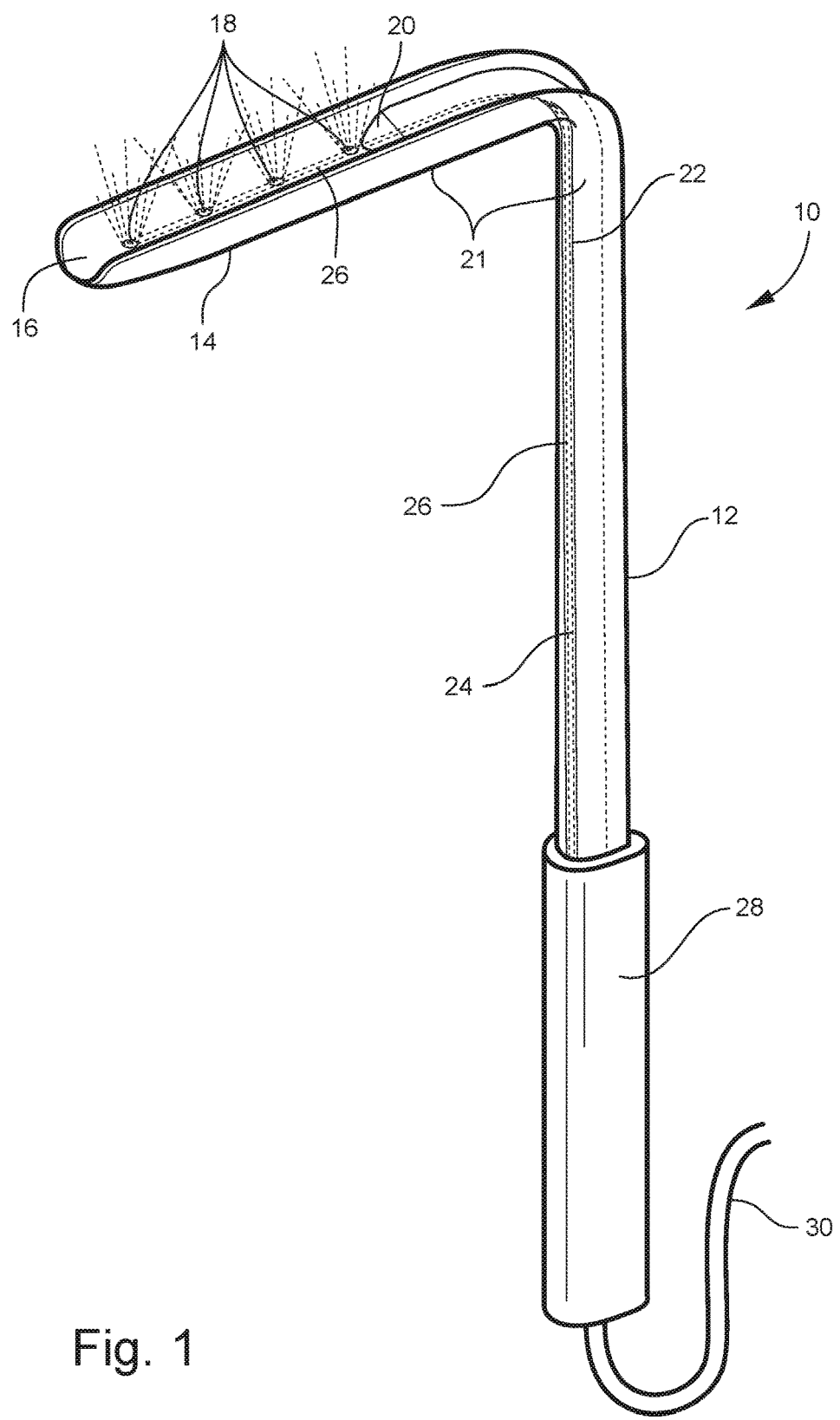
FIG. 1 is an illustration of a first embodiment of the present invention.

Referring to the figures, where like numerals refer to like elements, there is shown in FIG. 1 a first embodiment of the surgical retractor 10. Retractor 10 has a shaft 12 and a blade 14. Shaft 12 and blade 14 are joined together at an angle, are integral, and the angle may be adjustable (that is the angle between the blade and the shaft may be changed by, for example, bending by hand or by the inclusion of a pivoting mechanism (not shown)). In this embodiment, the angle may be 90° (but may be at other angles, e.g., 45-135°, or 55-115°, or 55-85°). Additionally, shaft 12 may be telescoping (not shown), so that it's length may be changed. The material may be opaque (i.e., non-light transmitting or non-transparent). The blade and shaft may be made of any material, metal or plastic. The material may be chosen so that the retractor may be sterilized by a variety of methods including, but not limited to, autoclaving, ethylene oxide, radiation, cold sterilization (i.e. hydrogen peroxide plasma), immersion sterilization (i.e. Cidex), or a combination thereof. The plastics may be: polyolefins (e.g., polypropylene, ultra high molecular weight polyethylene), polyamides, perfluoroelastomers, polycarbonates, polyetheretherketones (PEEKs), polyphenyl sulfones, acetals, and/or thermoplastic elastomers (e.g., EDPM rubber crosslinked with polypropylene). One such material may be ULTEM HU1004 (PEEK) available from Sabic Innovative Plastics of Pittsfield, Mass. In one embodiment of the present invention, the surgical retractor may be a single use device which is disposable.

The blade 14 has an upper surface 16 that may be concave, flat, round or convex. A plurality (at least two) of LED (light emitting diode) lights 18 may be disposed along the longitudinal axis of the blade 14. In this embodiment, four lights 18 are shown in-line along the axis; however, other configurations of these lights are possible (e.g., multiple rows and/or columns or other geometric configurations). The LED lights 18 face up from the upper surface 16. Face up as used herein means that the major axis of the LED light may be at any angle from 1 to 179° (or 45 to 135°) from the plane of the upper surface 16. The LED lights 18 may each face up at differing angles. In one embodiment of the present invention, the blade 14 may have a single LED light 18 disposed along the longitudinal axis of the blade 14. In another embodiment of the present invention, the blade 14 has an upper surface 16 that may be concare, flat, round or convex. One or more LED lights 18 may be disposed along the longitudinal or transverse axis of the blade 14.

A second surface 20 may also be associated with the upper surface 16 and is located on that portion of the upper surface 16 closer to the shaft 12. This second surface 20 is disposed on the upper surface 16 at an angle and is located behind the LED lights 18. The angle may be such that second surface 20 faces away from the upper surface 16.

The shaft 12 and the blade 14 have a common lower surface 21. A channel 22 is cut into the lower surface 21 of the blade 14 and the shaft 12. The channel 22 houses electrical connectors 26 (for example, see FIG. 3) that connect the LED lights 18 with a power source. The channel 22 is closed and sealed with a closure member 26. The closure member 24 may be flush with the lower surface 21. The closure member 26 may be selected from the group including but not limited to an adhesive, a screw, fastener, or snap on mechanism, or a combination thereof. The closure member 24 may be sealed in the channel 22 by use of an adhesive. The adhesive may be any adhesive, it may be sterilized by a variety of methods including, but not limited to, autoclaving, ethylene oxide, radiation, cold sterilization (i.e. hydrogen peroxide plasma), immersion sterilization (i.e. Cidex), or a combination thereof. Such adhesives may be epoxies or polyurethanes. One such adhesive maybe Loctite's HYSOL M-21HP or M-121HP available from Henkel Corporation of Rocky Hill, Conn.

The lower surface of the blade (not shown) may also have either a smooth surface or a gripping surface. The gripping surface may be used to maintain the retractor in place when inserted into the patient. The gripping surface (e.g., non-skid) may be, for example, roughened or ribbed.

In the first embodiment 10, the electrical connectors 26 may be in communication with a cord 30 that is used to connect with a remote power source, as will be understood by those of ordinary skill. Alternatively, the first embodiment may be battery powered as discussed below with regard to the second embodiment (and all of the variants of the second embodiment, discussed below, may be incorporated with the first embodiment).

A gripping surface 28 is located at the lower end of the shaft 12. The gripping surface 28 may be adapted for gripping by hand or with clamps.

Figure 2:
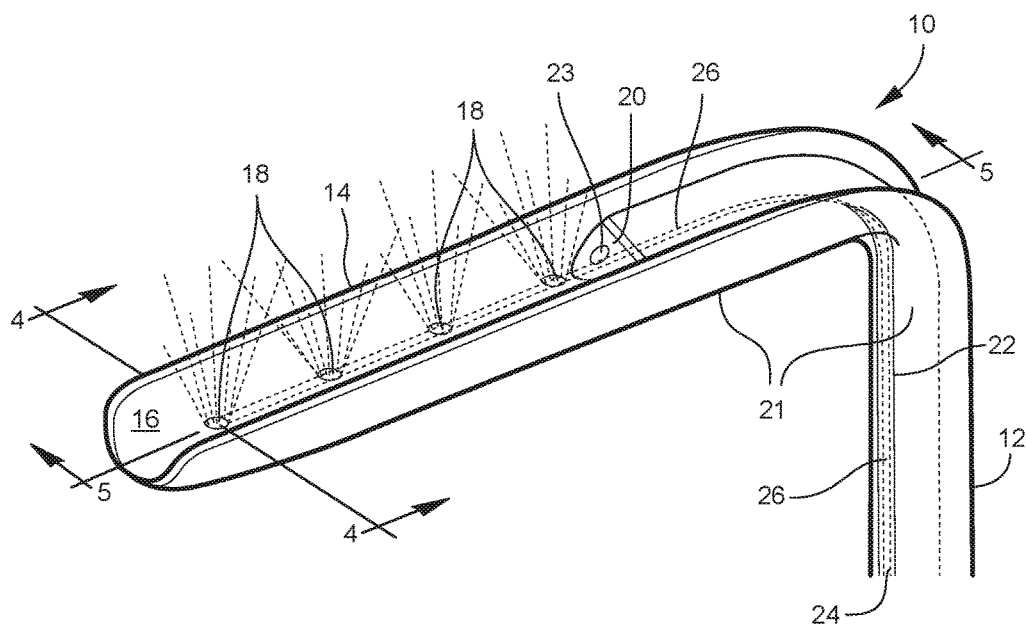
FIG. 2 is an enlarged illustration of a part of the first embodiment.
Figure 4:
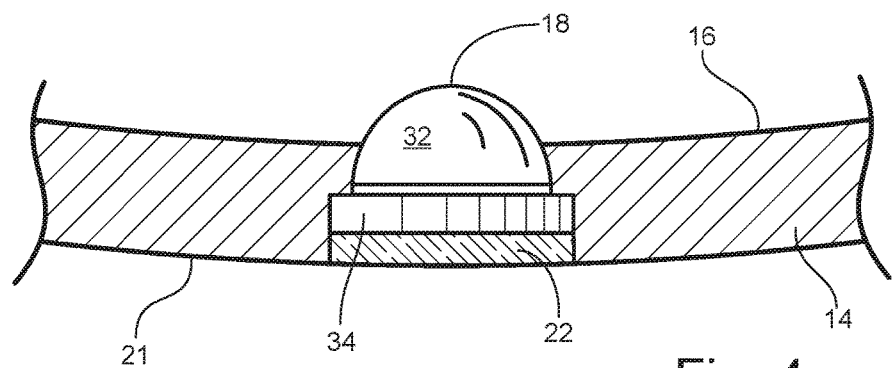
FIG. 4 is a sectional view taken along section lines 4-4 of FIG. 2.
Figure 5:
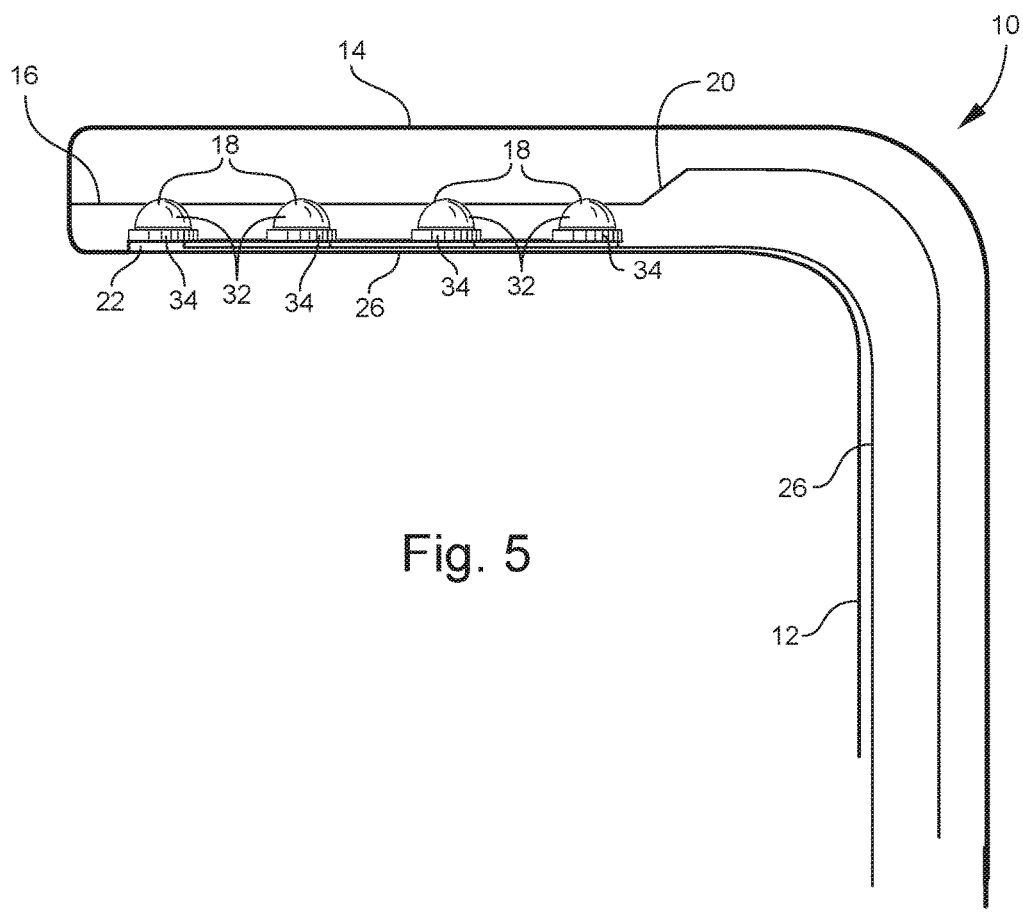
FIG. 5 is a sectional view taken along section lines 5-5 of FIG. 2.

Referring to FIGS. 2, 4, and 5, the placement of LED lights 18 is explained. In FIG. 4, LED light 18 has a lens 32 mounted on a base 34. At least a portion of the lens 32 of the LED light 18 may be exposed at surface 16. The outer surface of the lens 32 may be flush with upper surface 16 or may protrude above upper surface 16 (as shown in FIGS. 4 and 5). The LED light 18 is sealed within the blade 14 and there is no cover or blade material enclosing the LED light 18. The base 34 may be contained within channel 22. The electrical connectors 26 may be attached to the base 34.

The LED light 18 may be sealed in the channel 22 by use of an adhesive, screws, fasteners or a snap-on mechanism. The adhesive may be any adhesive, it may be sterilized by a variety of methods including, but not limited to, autoclaving, ethylene oxide, radiation, cold sterilization (i.e. hydrogen peroxide plasma), immersion sterilization (i.e. Cidex), or a combination thereof. Such adhesives may be epoxies or polyurethanes. One such adhesive maybe Loctite's HYSOL M-21HP or M-121HP available from Henkel Corporation of Rocky Hill, Conn.

In one embodiment of the present invention, the LED light or lights 18 may be mounted on a PCB board with built in circuitry. The PCB board may be either rigid or flexible, depending on the curvature requirement of where the LED lights are mounted on the PCB board. The PCB board may then be attached to the blade with an adhesive, screws, fasteners, or simply snap in place (see above for sterilization requirements). The PCB board may then be used to place LED lights 18 along either longitudinal axis, transverse axis, or a combination thereof as needed in the case of hook type retractor or in the convex, square, rectangle, or round shaped retractors. In another embodiment of the present invention, one or more LED lights 18 may be placed along either longitudinal axis, transverse axis, or a combination thereof as needed in the case of hook type retractor or in the convex, square, rectangle, or round shaped retractors without using the PCB board.

The LED lights 18 may produce at least 90 lumens (or at least 180 lumens of light). The LED lights 18 may be autoclaveable. The LED lights 18 may be on a dimmer switch. The LED light may be a LUXEON Rebel LXML-PWC1-0090 available from Philips Lumileds Lighting Co. of San Jose, Calif.

Figure 3:
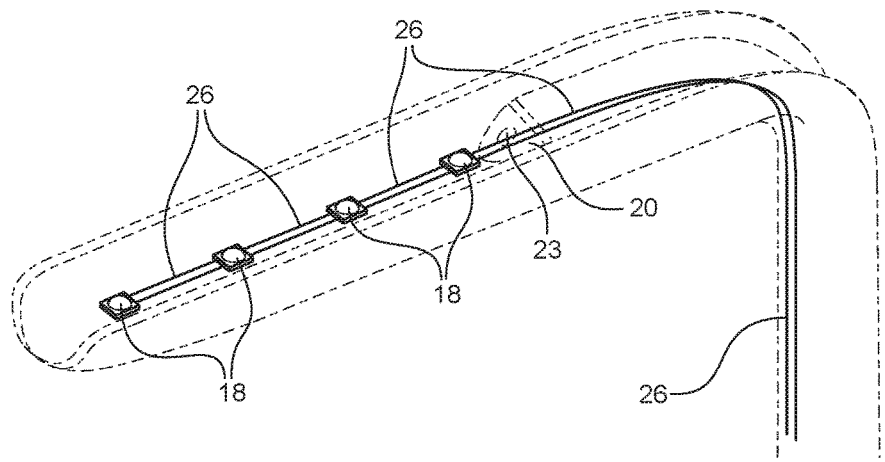
FIG. 3 is an enlarged illustration of the first embodiment with parts shown in phantom to illustrate certain internal components.

A camera 23 may be included in the retractor 10 (see FIGS. 2 and 3). Camera 23 may be a still camera or a motion camera. This camera may be based upon CCD (charged-coupled device) technology. In this embodiment, the camera 23 may be placed in the blade 14 on the second surface 20 behind LED lights 18. In this placement, the camera's field of vision is directed generally down the length of blade 14 and angled away from the upper surface 16, so that the camera 23 is looking at the operative field. This angle (as measured from behind surface 20) may be from 5-90°, or 15-80°, or 30-75°. Thus, the LED lights 18 illuminate, while the camera 23 sees the illuminated area. The camera 23 may transmit/store images in any fashion, i.e., via cable, or wireless transmission, or retained in a memory device for later retrieval. In one embodiment of the present invention, the CCD can be mounted anywhere along the upper surface 16 on the blade 14 either flush with the blade 14 or on a raised surface.

Figure 6:
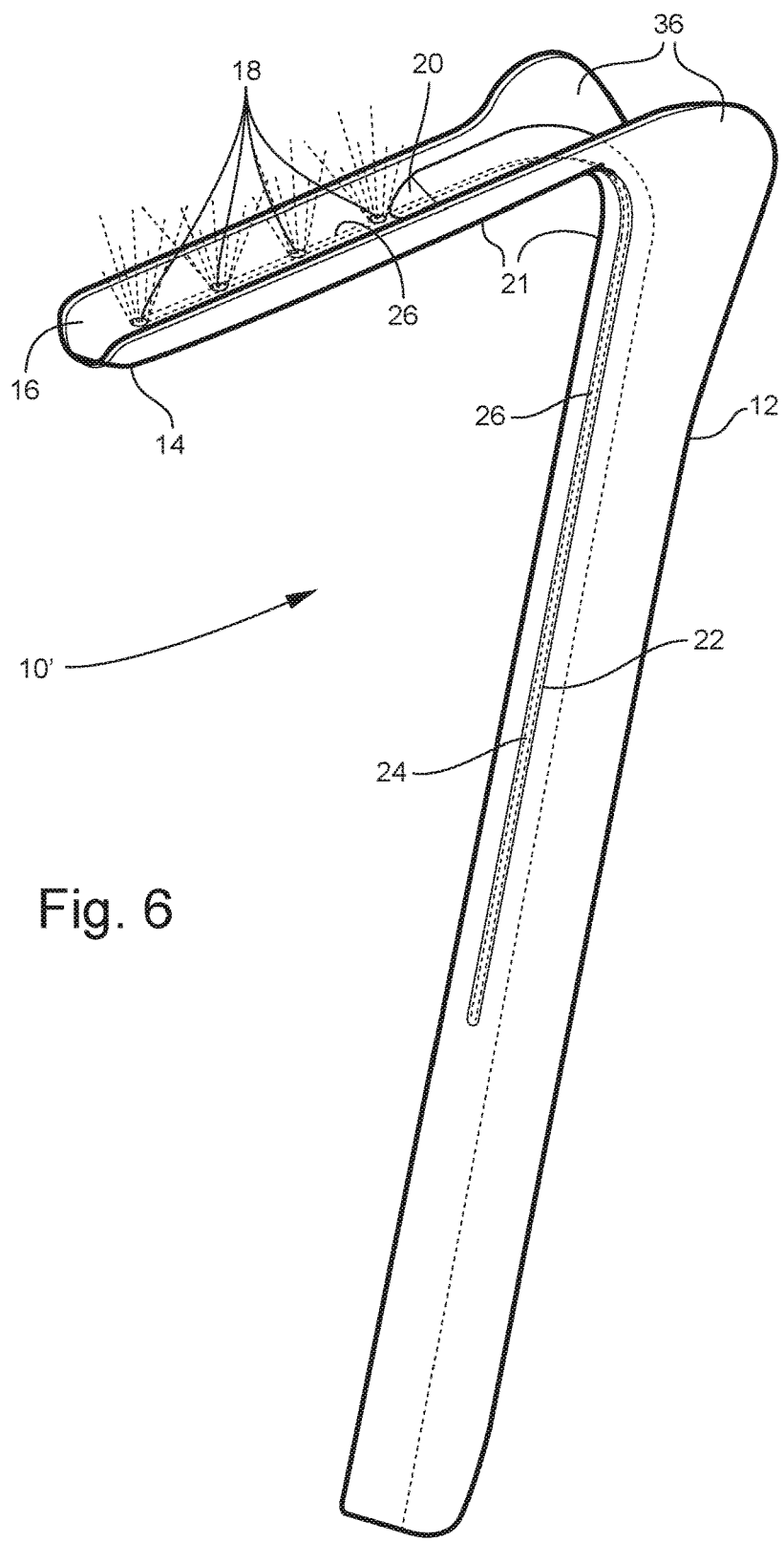
FIG. 6 is an illustration of a second embodiment of the present invention.
Figure 7:
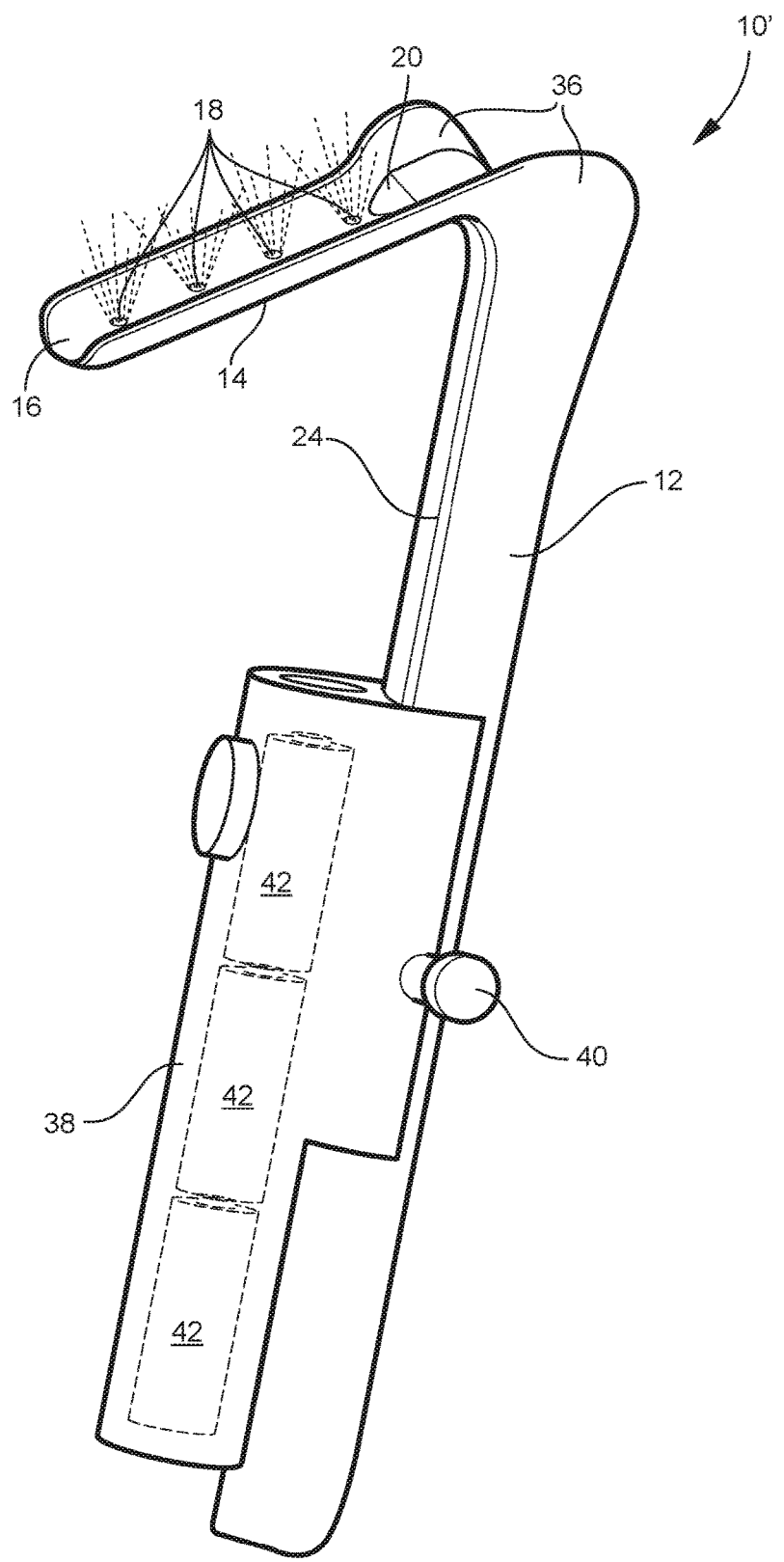
FIG. 7 is an illustration of the second embodiment with a power source attached thereto.

Referring to FIGS. 6 and 7, a second embodiment of the surgical retractor 10' is shown. Generally, second embodiment 10' is similar to first embodiment 10; accordingly, the discussion of the first embodiment 10 is included herein. This embodiment may be used 'hands-free,' that is the retractor remains in place without additional securement (hand-held or mechanical) by the weight of the retractor when the blade is inserted into an orifice (such as a vagina or an anus).

Surgical retractor 10' has a shaft 12 and a blade 14. Shaft 12 and blade 14 are joined together at an angle, are integral, and the angle may be adjustable (that is the angle between the blade and the shaft may be changed by, for example, bending by hand or by a pivoting mechanism (not shown)). Additionally, a pair of re-enforcing wings 36 may be located at the intersection of the shaft 12 and the blade 14. In this embodiment, the angle may be 45-135°, or 55-115°, or 55-85° (but may be at other angles, e.g., 90°). Additionally, shaft 12 may be telescoping (not shown), so that it's length may be changed. The blade and shaft may be made of any material, metal or plastic. This material may be opaque (i.e., non-light transmitting or non-transparent). The material may be chosen so that the retractor can be sterilized by a variety of methods including, but not limited to, autoclaving, ethylene oxide, radiation, cold sterilization (i.e. hydrogen peroxide plasma), immersion sterilization (i.e. Cidex), or a combination thereof. The plastics may be: polyolefins (e.g., polypropylene, ultra high molecular weight polyethylene), polyamides, perfluoroelastomers, polycarbonates, polyetheretherketones (PEEKs), polyphenyl sulfones, acetals, and/or thermoplastic elastomers (e.g., EDPM rubber crosslinked with polypropylene). One such material may be ULTEM HU1004 (PEEK) available from Sabic Innovative Plastics of Pittsfield, Mass.

The blade 14 has an upper surface 16 that may be concave (or flat or convex). A plurality (at least two) of LED (light emitting diode) lights 18 may be disposed along the longitudinal axis of the blade 14. In this embodiment, four lights 18 are shown in-line along the axis; however, other configurations of these lights are possible (e.g., multiple rows and/or columns or other geometric configurations). The LED lights 18 face up from the upper surface 16. Face up as used herein means that the major axis of the LED light may be at any angle from 1 to 179° (or 45 to 135°) from the plane of the upper surface 16. The LED lights 18 may each face up at differing angles. Further, details on the placement of the LED lights 18 may be found in the discussion of FIGS. 2-5 above. In one embodiment of the present invention, the blade 14 may have a single LED light 18 disposed along the longitudinal axis of the blade 14. In another embodiment of the present invention, the blade 14 has an upper surface 16 that may be concare, flat, round or convex. One or more LED lights 18 may be disposed along the longitudinal or transverse axis of the blade 14.

A second surface 20 may also be associated with the upper surface 16 and is located on that portion of the upper surface 16 closer to the shaft 12. This second surface 20 is disposed on the upper surface 16 at an angle and is located behind the LED lights 18. The angle may be such that second surface 20 faces away from the upper surface 16.

The shaft 12 and the blade 14 have a common lower surface 21. A channel 22 is cut into the lower surface 21 of the blade 14 and the shaft 12. The channel 22 houses electrical connectors 26 (for example, see FIG. 3) that connect the LED lights 18 with a power source. The channel 22 is closed and sealed with a closure member 26. The closure member 26 may be flush with the lower surface 21. The closure member 26 may be sealed in the channel 22 by use of an adhesive, screws, fasteners, or snap-on mechanism. The adhesive may be any adhesive, it may be sterilized by a variety of methods including, but not limited to, autoclaving, ethylene oxide, radiation, cold sterilization (i.e. hydrogen peroxide plasma), immersion sterilization (i.e. Cidex), or a combination thereof. Such adhesives may be epoxies or polyurethanes. One such adhesive maybe Loctite's HYSOL M-21HP or M-121HP available from Henkel Corporation of Rocky Hill, Conn.

The lower surface of the blade (not shown) may also have either a smooth surface or a gripping surface. The gripping surface may be used to maintain the retractor in place when inserted into the patient. The gripping surface (e.g., non-skid) may be, for example, roughened or ribbed.

In the second embodiment 10', the electrical connectors 26 are in communication with a power source 38 removeably mounted on shaft 12. Power source 38 may contain batteries 42 and may be removeably mounted onto shaft 12 via a clamp 40. Additionally, this power source provides a weight, so that the retractor 10' may be used hands-free, as discussed above. Furthermore, this power source 38 is removable from shaft 12. Thus, retractor 10' may be autoclaved without the power source 38. Power source 38 may be autoclaved without the batteries 42. In this situation, a sterile sleeve (not shown) may be used to insert batteries 42 into the sterile power source 38.

A camera (not shown), as discussed above, may be included in the retractor 10'. This camera may be a still camera or a motion camera. This camera may be based upon CCD (charged-coupled device) technology. In this embodiment, the camera may be placed in the blade 14 on the second surface 20 behind LED lights 18. In this placement, the camera's field of vision is directed generally down the length of blade 14 and angled away from the upper surface 16, so that the camera 23 is looking at the operative field. This angle (as measured from behind surface 20) may be from 5-90°, or 15-80°, or 30-75°. Thus, the LED lights 18 illuminate, while the camera 23 sees the illuminated area. The camera 23 may transmit/store images in any fashion, i.e., via cable, or wireless transmission, or retained in a memory device for later retrieval. In one embodiment of the present invention, the CCD can be mounted anywhere along the upper surface 16 on the blade 14 either flush with the blade 14 or on a raised surface.

Additional variants of the second embodiment (not shown) may include: the battery source permanently fixed to the retractor; the battery source and retractor being a single, integral unit; a remote power source (as described above) with a removable weight; a remote power source (as described above) with a non-removable weight.

Figure 8:
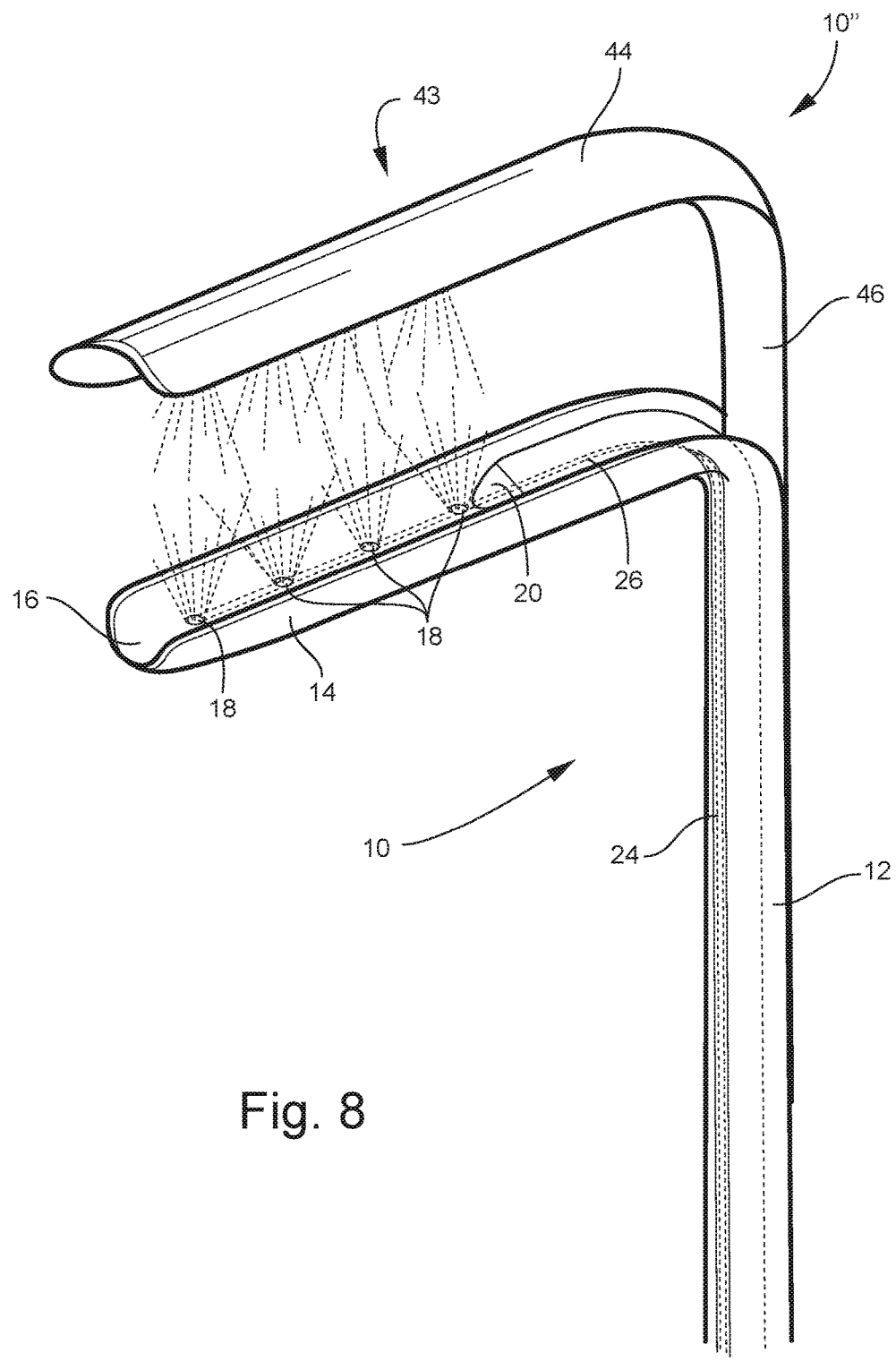
FIG. 8 is an illustration of a third embodiment of the present invention.

Referring to FIG. 8, a third embodiment of the surgical retractor 10" is shown. All of the features of the first embodiment 10 and the second embodiment 10' may be included in the third embodiment 10". The third embodiment 10" may be generally referred to as the speculum embodiment. Retractor 10" includes retractor 10 and a second arm 43 moveably affixed to retractor 10. Retractor 10 may be the same as previously described retractors 10 and/or 10'; accordingly, further detail discussion may be found above.

The second arm 43 includes a second shaft 46 joined to second blade 44. Construction of these mating shafts should be such that visualization by the medical professional is not unduly obstructed. In this regard, reference is made to a standard 'duck bill' speculum, incorporated herein by reference. Second arm 43 may be moveable along shaft 12 of retractor 10, so that blades 14 and 44 may be spaced apart. Further, blades 14 and 44 may be hinged (not shown) on shafts 12 and 46, respectively; so that the distal tips of blades 14 and 44 may be spread apart further than the hinged portions of the blades 14 and 44. Blade 44 is shown as having a concave surface with LED lights, but other configurations are possible (e.g., no lights and no concave surface).

Figure 9:
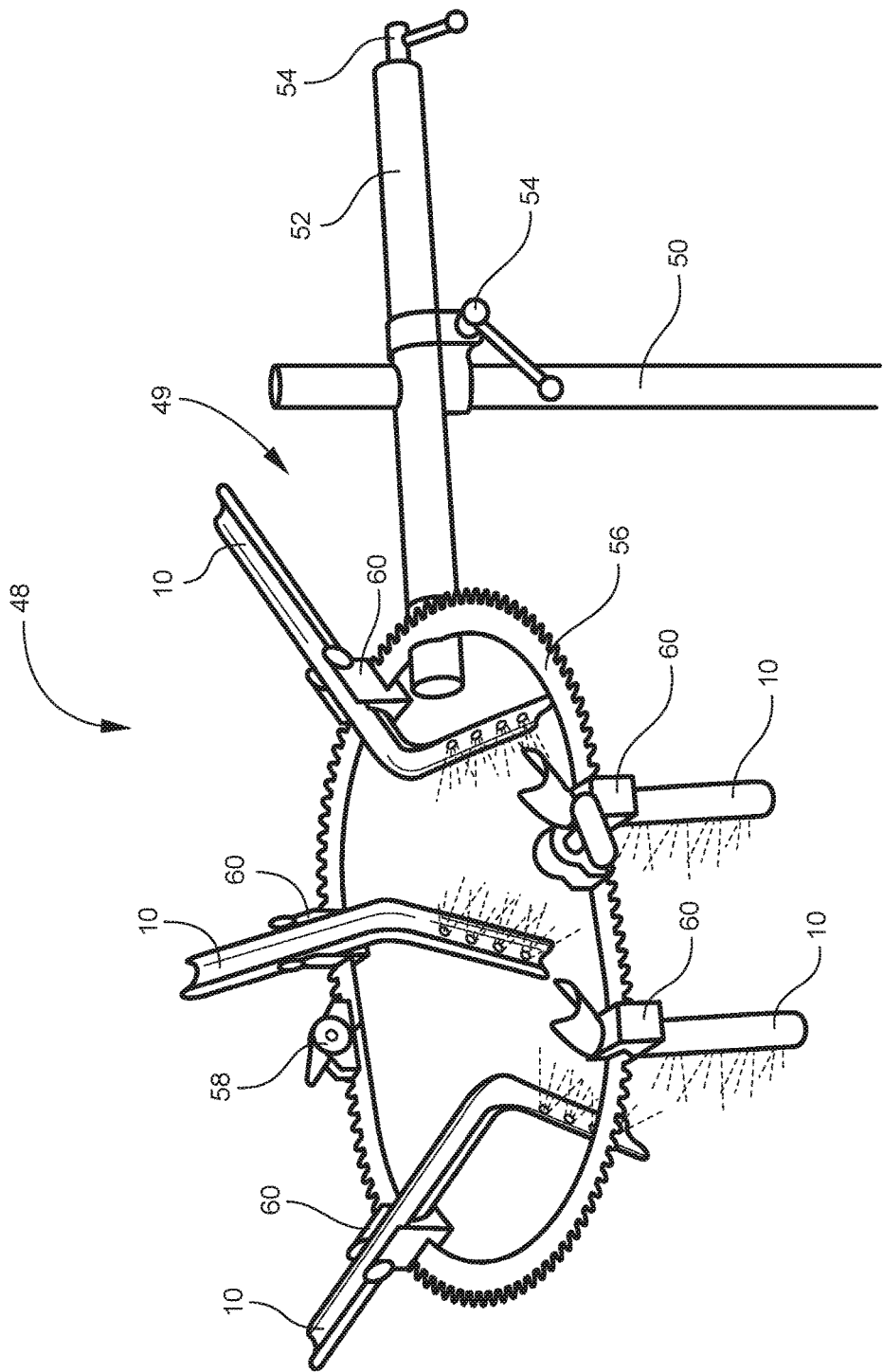
FIG. 9 is an illustration of a fourth embodiment of the present invention.

Referring to FIG. 9, a fourth embodiment, a surgical retractor kit 48 is shown. All of the features of the first embodiment 10, the second embodiment 10', and the third embodiment 10" may be included in the surgical retractor kit 48. The surgical retractor kit 48 may be generally referred to as a self retaining retractor system. The surgical retractor kit 48 generally includes a plurality (at least two) retractors 10

(previously discussed retractor 10' may used instead), and a holder set 49. Holder set 49 may include a stand 50, arm 52, clamps 54 for fixing and securing the stand 50 and arm 52 in place, mounting ring 56 for placement of the retractors 10, ring clamp 58, and couplers 60 for fixing the retractors in place on mounting ring 56.

Figure 10:
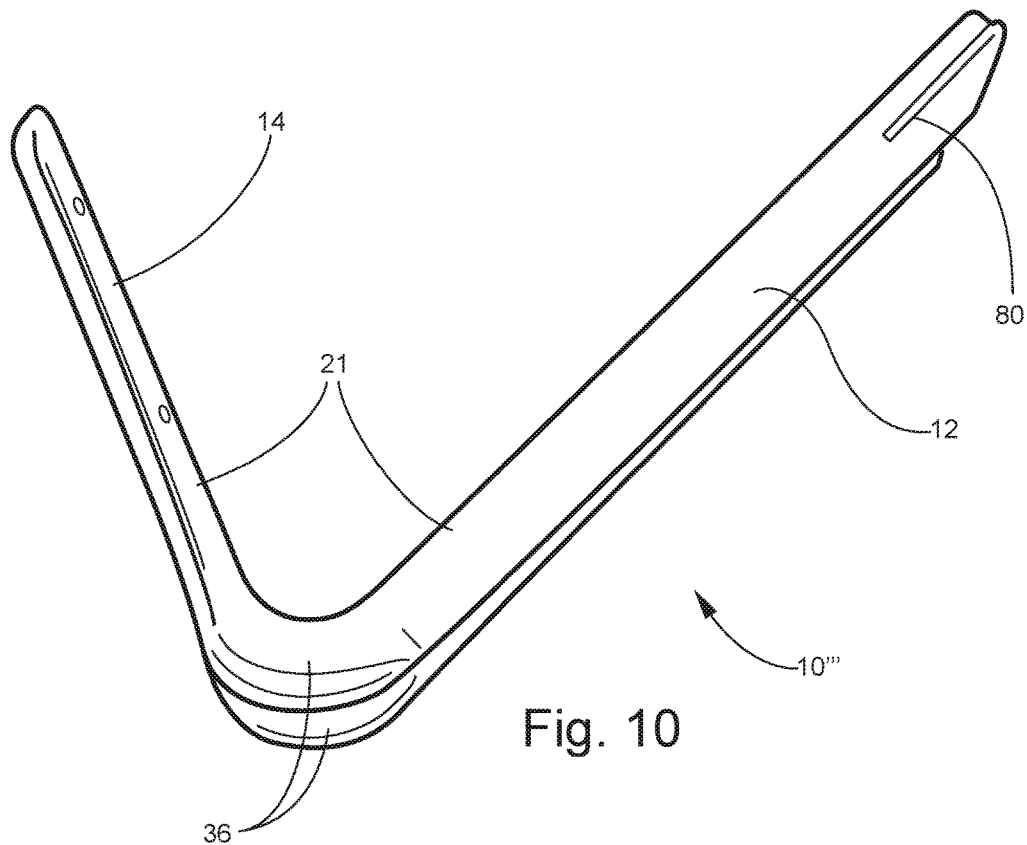
FIG. 10 is an illustration of a fifth embodiment of the present invention.
Figure 11:
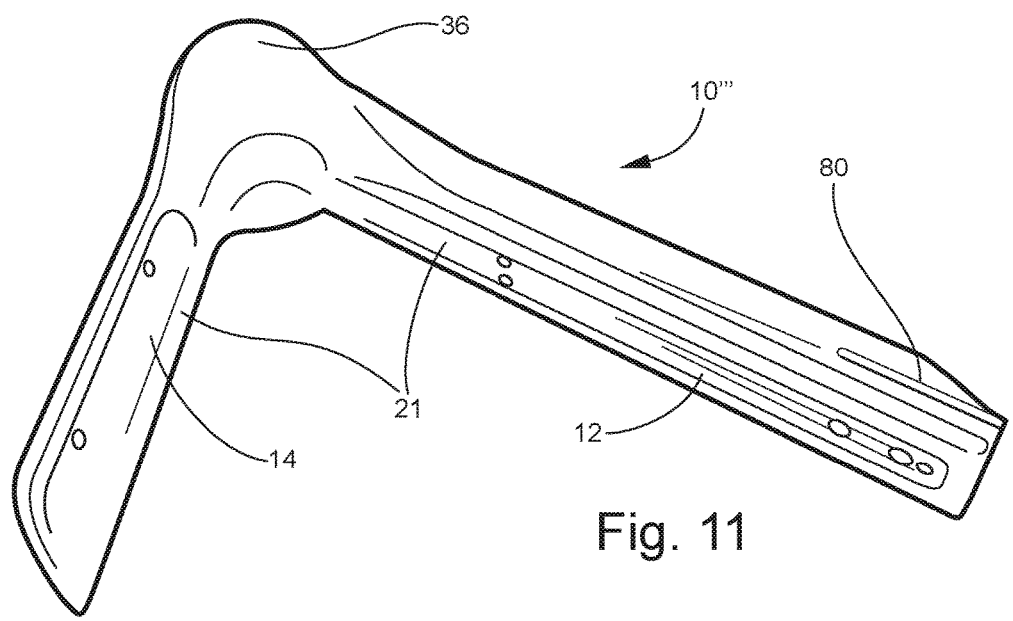
FIG. 11 is an illustration of a fifth embodiment of the present invention.

Referring to FIGS. 10 and 11, a fifth embodiment of the surgical retractor is shown. All of the features of the previous embodiments may be included in the fifth embodiment. This embodiment illustrates a surgical retractor 10''' which has a shaft 12 and a blade 14. Shaft 12 and blade 14 are joined together at an angle, are integral, and the angle may be adjustable (that is the angle between the blade and the shaft may be changed by, for example, bending by hand or by a pivoting mechanism (not shown)). Additionally, a pair of re-enforcing wings 36 may be located at the intersection of the shaft 12 and the blade 14. In this embodiment, the angle may be 45-135°, or 55-115°, or 55-85° (but may be at other angles, e.g., 90°). Additionally, shaft 12 may be telescoping (not shown), so that it's length may be changed. The blade and shaft may be made of any material, metal or plastic. This material may be opaque (i.e., non-light transmitting or non-transparent). The material may be chosen so that the retractor can be sterilized by a variety of methods including, but not limited to, autoclaving, ethylene oxide, radiation, cold sterilization (i.e. hydrogen peroxide plasma), immersion sterilization (i.e. Cidex), or a combination thereof. The plastics may be: polyolefins (e.g., polypropylene, ultra high molecular weight polyethylene), polyamides, perfluoroelastomers, polycarbonates, polyetheretherketones (PEEKs), polyphenyl sulfones, acetals, and/or thermoplastic elastomers (e.g., EDPM rubber crosslinked with polypropylene). One such material may be ULTEM HU1004 (PEEK) available from Sabic Innovative Plastics of Pittsfield, Mass.

The blade 14 has an upper surface 16 that may be concave (or flat or convex). A plurality (at least two) of LED (light emitting diode) lights 18 may be disposed along the longitudinal axis of the blade 14. In this embodiment, four lights 18 are shown in-line along the axis; however, other configurations of these lights are possible (e.g., multiple rows and/or columns or other geometric configurations). The LED lights 18 face up from the upper surface 16. Face up as used herein means that the major axis of the LED light may be at any angle from 1 to 179° (or 45 to 135°) from the plane of the upper surface 16. The LED lights 18 may each face up at differing angles. Further, details on the placement of the LED lights 18 may be found in the discussion of FIGS. 2-5 above. In one embodiment of the present invention, the blade 14 may have a single LED light 18 disposed along the longitudinal axis of the blade 14. In another embodiment of the present invention, the blade 14 has an upper surface 16 that may be concare, flat, round or convex. One or more LED lights 18 may be disposed along the longitudinal or transverse axis of the blade 14.

A second surface 20 may also be associated with the upper surface 16 and is located on that portion of the upper surface 16 closer to the shaft 12. This second surface 20 is disposed on the upper surface 16 at an angle and is located behind the LED lights 18. The angle may be such that second surface 20 faces away from the upper surface 16.

The shaft 12 and the blade 14 have a common lower surface 21. A channel 22 is cut into the lower surface 21 of the blade 14 and the shaft 12. The channel 22 houses electrical connectors 26 (for example, see FIG. 3) that connect the LED lights 18 with a power source. The channel 22 is closed and sealed with a closure member 26. The closure member 24 may be flush with the lower surface 21.

The closure member 26 may be sealed in the channel 22 by use of an adhesive, screws, fasteners, or snap-on mechanism. The adhesive may be any adhesive, it may be sterilized by a variety of methods including, but not limited to, autoclaving, ethylene oxide, radiation, cold sterilization (i.e. hydrogen peroxide plasma), immersion sterilization (i.e. Cidex), or a combination thereof. Such adhesives may be epoxies or polyurethanes. One such adhesive maybe Locite's HYSOL M-21HP or M-121HP available from Henkel Corporation of Rocky Hill, Conn. The blade 14 also includes a ridge 80 which may be used when attaching to a power source 38.

The lower surface of the blade (not shown) may also have either a smooth surface or a gripping surface. The gripping surface may be used to maintain the retractor in place when inserted into the patient. The gripping surface (e.g., non-skid) may be, for example, roughened or ribbed.

In the fifth embodiment 10''', the electrical connectors 26 are in communication with a power source 38 removeably mounted on shaft 12. Power source 38 may contain batteries 42 and may be removeably mounted onto shaft 12 via a clamp 40. Additionally, this power source provides a weight, so that the retractor 10''' may be used hands-free, as discussed above. Furthermore, this power source 38 is removable from shaft 12. Thus, retractor 10''' may be autoclaved without the power source 38. Power source 38 may be autoclaved without the batteries 42. In this situation, a sterile sleeve (not shown) may be used to insert batteries 42 into the sterile power source 38.

A camera (not shown), as discussed above, may be included in the retractor 10'''. This camera may be a still camera or a motion camera. This camera may be based upon CCD (charged-coupled device) technology. In this embodiment, the camera may be placed in the blade 14 on the second surface 20 behind LED lights 18. In this placement, the camera's field of vision is directed generally down the length of blade 14 and angled away from the upper surface 16, so that the camera 23 is looking at the operative field. This angle (as measured from behind surface 20) may be from 5-90°, or 15-80°, or 30-75°. Thus, the LED lights 18 illuminate, while the camera 23 sees the illuminated area. The camera 23 may transmit/store images in any fashion, i.e., via cable, or wireless transmission, or retained in a memory device for later retrieval. In one embodiment of the present invention, the CCD can be mounted anywhere along the upper surface 16 on the blade 14 either flush with the blade 14 or on a raised surface.

Additional variants of the fifth embodiment (not shown) may include: the battery source permanently fixed to the retractor; the battery source and retractor being a single, integral unit; a remote power source (as described above) with a removable weight; a remote power source (as described above) with a non-removable weight.

Figure 12:
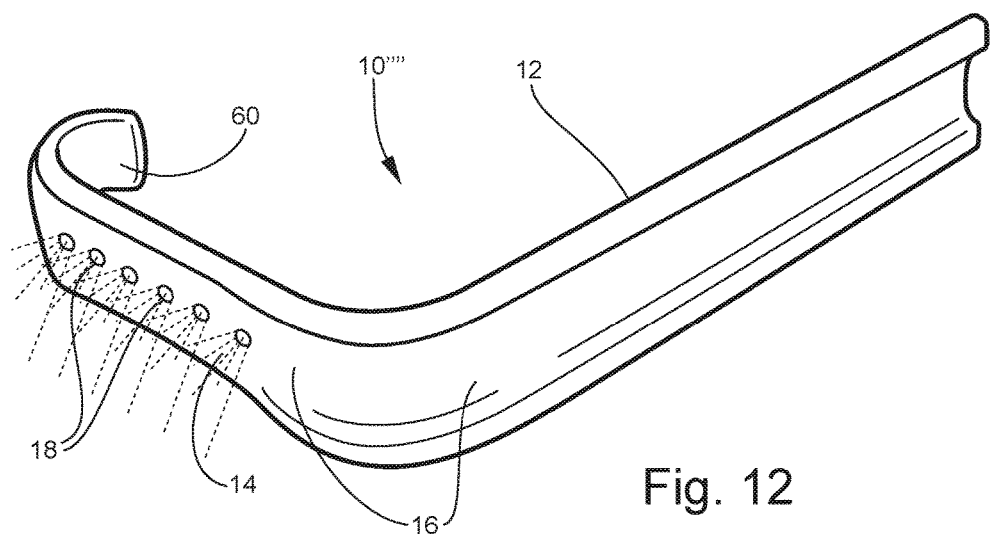
FIG. 12 is an illustration of a sixth embodiment of the present invention.
Figure 13:
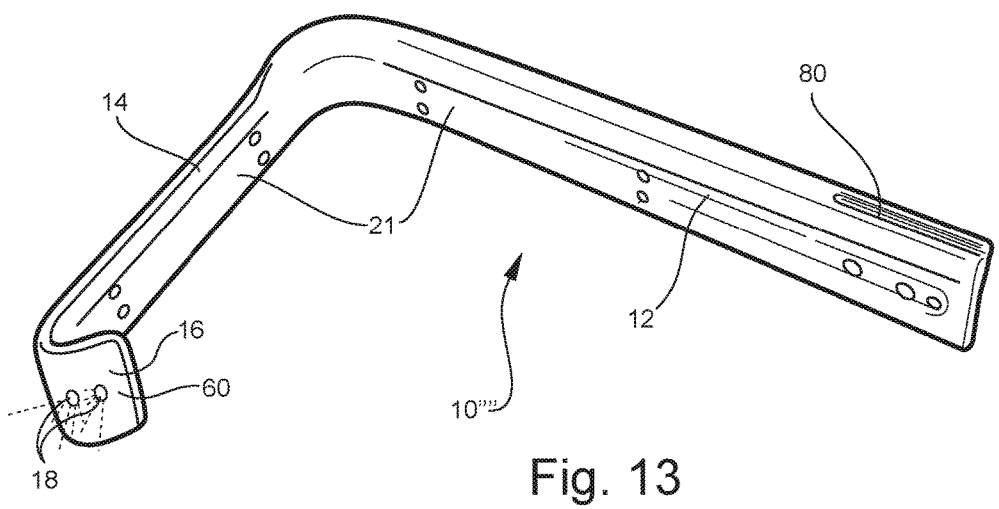
FIG. 13 is an illustration of a sixth embodiment of the present invention.

Referring to FIGS. 12 and 13, a sixth embodiment of the surgical retractor is shown. All of the features of the previous embodiments may be included in the sixth embodiment. This embodiment illustrates a surgical retractor 10'''' which has a shaft 12 and a blade 14 with an extension on the end of the blade 14. This extension may be described as a hook 60 as illustrated in FIGS. 12 and 13. The shaft 12 and blade 14 are joined together at an angle, are integral, and the angle may be adjustable (that is the angle between the blade and the shaft may be changed by, for example, bending by hand or by a pivoting mechanism (not shown)). Additionally, a pair of re-enforcing wings 36 may be located at the intersection of the shaft 12 and the blade 14. In this embodiment, the angle may be 45-135°, or 55-115°, or 55-85° (but may be at other angles, e.g., 90°). Additionally, shaft 12 may be telescoping (not shown), so that it's length may be changed. The blade 14 and hook 60 are joined together at an angle, are integral, and the angle may be adjustable (that is the angle between the blade and the shaft may be changed by, for example, bending by hand or by a pivoting mechanism (not shown)). In this embodiment, the angle may be 45-135°, or 55-115°, or 55-85° (but may be at other angles, e.g., 90°). The blade, shaft and hook may be made of any material, metal or plastic. This material may be opaque (i.e., non-light transmitting or non-transparent). The material may be chosen so that the retractor can be sterilized by a variety of methods including, but not limited to, autoclaving, ethylene oxide, radiation, cold sterilization (i.e. hydrogen peroxide plasma), immersion sterilization (i.e. Cidex), or a combination thereof. The plastics may be: polyolefins (e.g., polypropylene, ultra high molecular weight polyethylene), polyamides, perfluoroelastomers, polycarbonates, polyetheretherketones (PEEKs), polyphenyl sulfones, acetals, and/or thermoplastic elastomers (e.g., EDPM rubber crosslinked with polypropylene). One such material may be ULTEM HU1004 (PEEK) available from Sabic Innovative Plastics of Pittsfield, Mass.

The blade 14 has an upper surface 16 that may be concave (or flat or convex). A plurality (at least two) of LED (light emitting diode) lights 18 may be disposed along the longitudinal axis of the blade 14. In this embodiment, four lights 18 are shown in-line along the axis; however, other configurations of these lights are possible (e.g., multiple rows and/or columns or other geometric configurations). The LED lights 18 face up from the upper surface 16. Face up as used herein means that the major axis of the LED light may be at any angle from 1 to 179° (or 45 to 135°) from the plane of the upper surface 16. The LED lights 18 may each face up at differing angles. Further, details on the placement of the LED lights 18 may be found in the discussion of FIGS. 2-5 above. In one embodiment of the present invention, the blade 14 may have a single LED light 18 disposed along the longitudinal axis of the blade 14. In another embodiment of the present invention, the blade 14 has an upper surface 16 that may be concare, flat, round or convex. One or more LED lights 18 may be disposed along the longitudinal or transverse axis of the blade 14.

The hook 60 may be disposed along the longitudinal axis of the blade 14. In this embodiment, two lights 18 are shown in-line along the longitudinal axis; however, other configurations of these lights are possible (e.g., transverse, multiple rows and/or columns or other geometric configurations). The LED lights face up from the surface of the hook. Face up as used herein means that the major axis of the LED light may be at any angle from 1 to 179° (or 45 to 135°) from the plane of the upper surface 16. The LED lights 18 may each face up at differing angles. Further, details on the placement of the LED lights 18 may be found in the discussion of FIGS. 2-5 above. The LED lights 18 located on the hook 60 may face in a different direction that the lights located on the upper surface 16 of the blade 14.

A second surface 20 may also be associated with the upper surface 16 and is located on that portion of the upper surface 16 closer to the shaft 12. This second surface 20 is disposed on the upper surface 16 at an angle and is located behind the LED lights 18. The angle may be such that second surface 20 faces away from the upper surface 16.

The hook 60, the shaft 12 and the blade 14 have a common lower surface 21. A channel 22 is cut into the lower surface 21 of the hook 60, the blade 14 and the shaft 12. The channel 22 houses electrical connectors 26 (for example, see FIG. 3) that connect the LED lights 18 with a power source. The channel 22 is closed and sealed with a closure member 26. The closure member 24 may be flush with the lower surface 21. The closure member 26 may be sealed in the channel 22 by use of an adhesive, screws, fasteners, or snap-on mechanism. The adhesive may be any adhesive, it may be sterilized by a variety of methods including, but not limited to, autoclaving, ethylene oxide, radiation, cold sterilization (i.e. hydrogen peroxide plasma), immersion sterilization (i.e. Cidex), or a combination thereof. Such adhesives may be epoxies or polyurethanes. One such adhesive maybe Locite's HYSOL M-21HP or M-121HP available from Henkel Corporation of Rocky Hill, Conn. The blade 14 also includes a ridge 80 which may be used when attaching to a power source 38.

The lower surface of the blade (not shown) may also have either a smooth surface or a gripping surface. The gripping surface may be used to maintain the retractor in place when inserted into the patient. The gripping surface (e.g., non-skid) may be, for example, roughened or ribbed.

In the sixth embodiment 10"", the electrical connectors 26 are in communication with a power source 38 removeably mounted on shaft 12. Power source 38 may contain batteries 42 and may be removeably mounted onto shaft 12 via a clamp 40. Additionally, this power source provides a weight, so that the retractor 10"" may be used hands-free, as discussed previously. Furthermore, this power source 38 is removable from shaft 12. Thus, retractor 10"" may be autoclaved without the power source 38. Power source 38 may be autoclaved without the batteries 42. In this situation, a sterile sleeve (not shown) may be used to insert batteries 42 into the sterile power source 38.

A camera (not shown), as discussed above, may be included in the retractor 10"". This camera may be a still camera or a motion camera. This camera may be based upon CCD (charged-coupled device) technology. In this embodiment, the camera may be placed in the blade 14 on the second surface 20 behind LED lights 18. In this placement, the camera's field of vision is directed generally down the length of blade 14 and angled away from the upper surface 16, so that the camera 23 is looking at the operative field. This angle (as measured from behind surface 20) may be from 5-90°, or 15-80°, or 30-75°. Thus, the LED lights 18 illuminate, while the camera 23 sees the illuminated area. The camera 23 may transmit/store images in any fashion, i.e., via cable, or wireless transmission, or retained in a memory device for later retrieval. In one embodiment of the present invention, the CCD can be mounted anywhere along the upper surface 16 on the blade 14 either flush with the blade 14 or on a raised surface.

Additional variants of the sixth embodiment (not shown) may include: the battery source permanently fixed to the retractor; the battery source and retractor being a single, integral unit; a remote power source (as described above) with a removable weight; a remote power source (as described above) with a non-removable weight.

Figure 14:
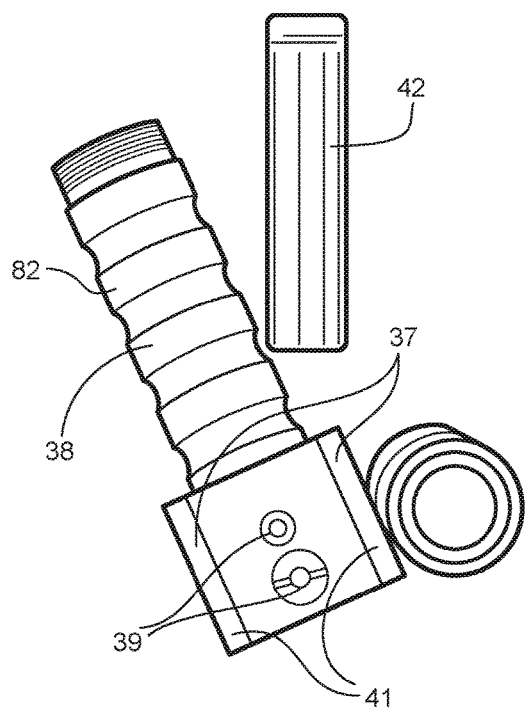
FIG. 14 is an illustration of a seventh embodiment of the present invention.
Figure 16:
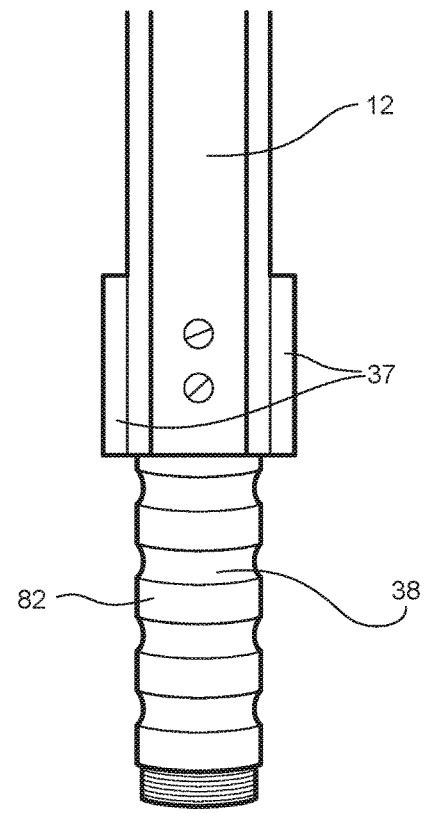
FIG. 16 is an illustration of a seventh embodiment of the present invention.
Figure 15:
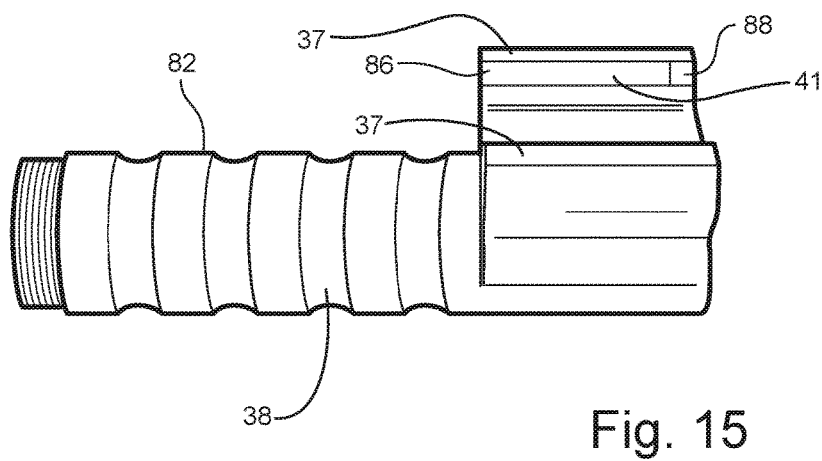
FIG. 15 is an illustration of a seventh embodiment of the present invention.
Figure 17:
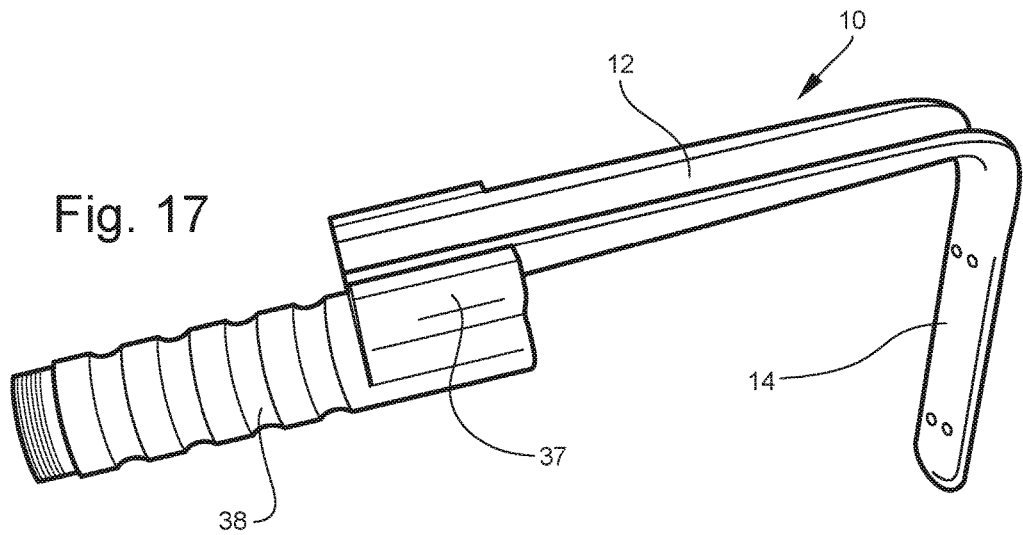
FIG. 17 is an illustration of a seventh embodiment of the present invention.
Figure 18:
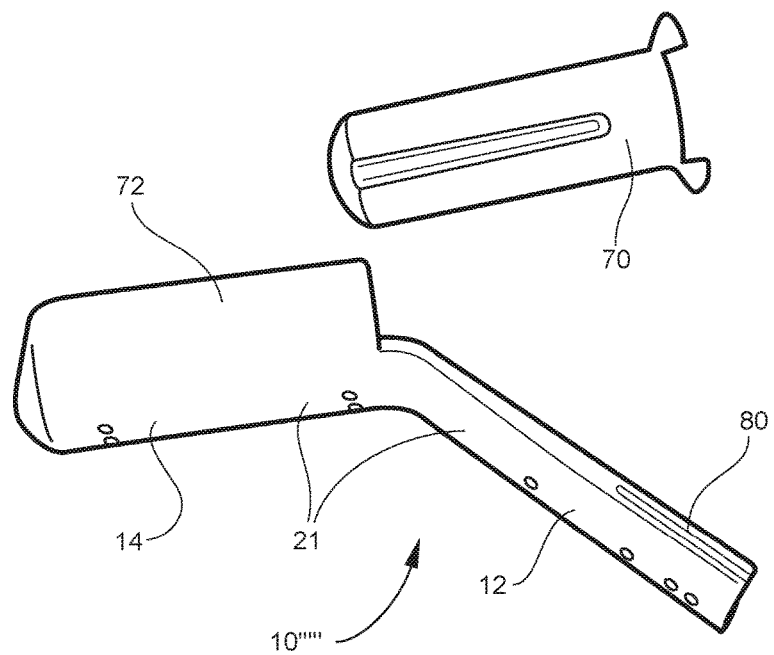
FIG. 18 is an illustration of a eighth embodiment of the present invention.
Figure 19:
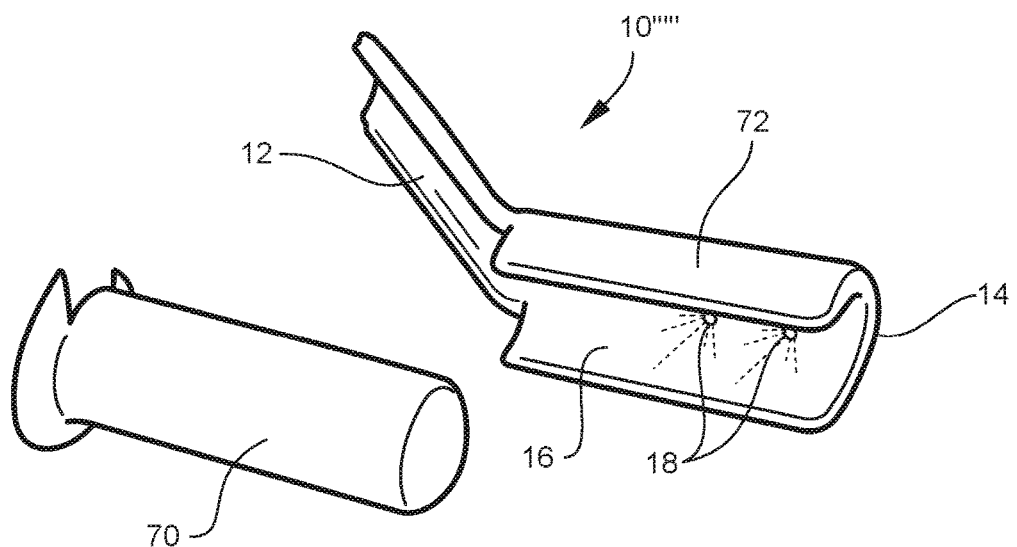
FIG. 19 is an illustration of a eighth embodiment of the present invention.

Referring to FIGS. 14-17, a seventh embodiment of the surgical retractor is shown. All of the features of the previous embodiments may be included in the seventh embodiment. FIGS. 14-17 illustrate a power source 38 which includes a handle 82 and a pair of extension arms 37 which emanate up from the main body of the power source. Each extension arm 37 provides housing for a slot 41 shown in FIGS. 14 & 15 and each slot 41 has an open end 86 near the handle 82 of the power source and a barrier 88 at the opposite end of the slot 41. Each slot 41 works in conjunction with one of the ridges 80 located on the shaft 12 of a surgical retractor. The shaft 12 is slideably engaged with the power source 38 by aligning the ridges 80 of the shaft with the open end 86 of each slot 41 and then guiding the ridges 80 within each slot 41 by sliding the shaft 12 away from the handle 82 portion of the power source 38. The barriers 88 located at the end of each slot 41 prevent the ridges 51 and the shaft 12 from exiting the slot 41 on the end opposite of the open end 86. This design allows the user of the surgical retractor the ability to retract tissue without any concern of the power source 38 disengaging from the shaft 12 as the surgical retractor is pulled while holding the handle 82. Also illustrated in FIG. 14 are a pair of electrical connectors which supply power from the battery 42 to the plurality of LED lights located within the blade 14 or blades of the surgical retractor. FIG. 17 illustrates a surgical retractor 10 in which the shaft 12 is fully engaged to the power source 38.

Figure 20:
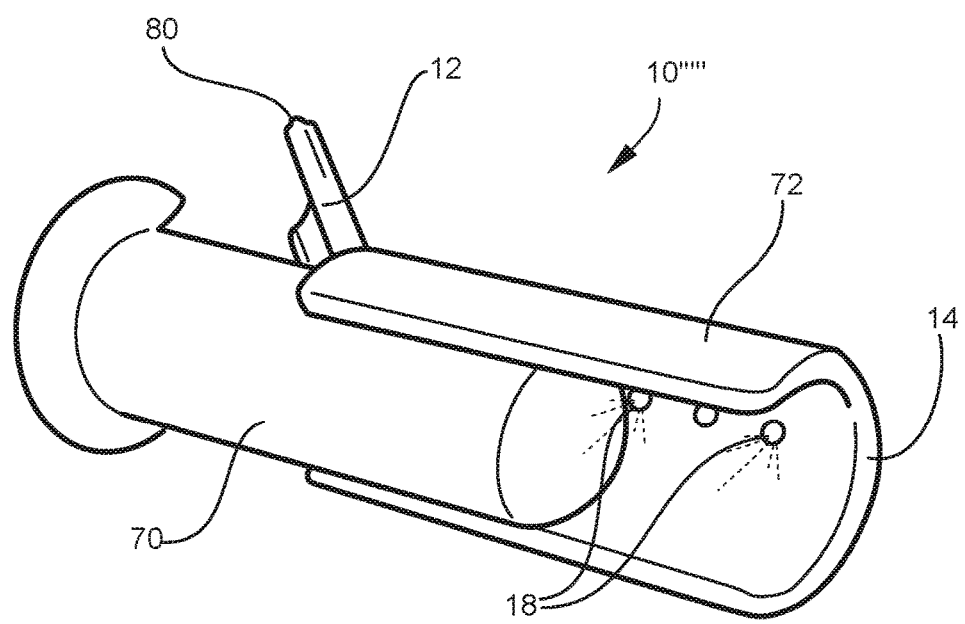
FIG. 20 is an illustration of a eighth embodiment of the present invention.
Figure 21:
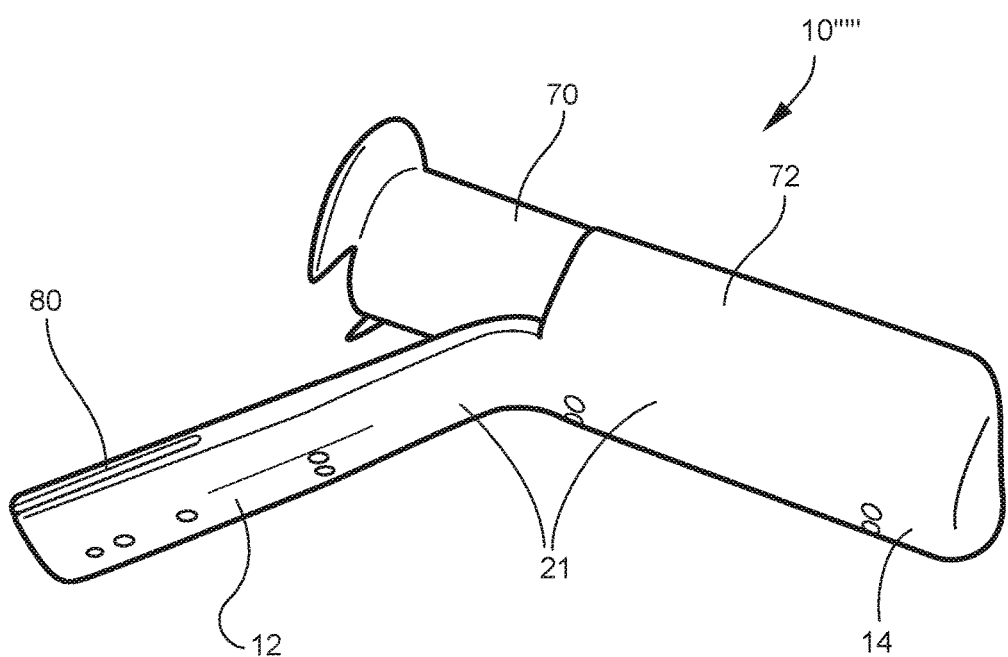
FIG. 21 is an illustration of a eighth embodiment of the present invention.

Referring to FIGS. 18-21, an eighth embodiment of the surgical retractor is shown. All of the features of the previous embodiments may be included in the eighth embodiment. The eighth embodiment 10'''' may be generally referred to a modified speculum embodiment. Retractor 10'''' includes retractor 10 and a sleeve 72 which emanates up from the blade 14 of the retractor. The sleeve 72 is shown in FIGS. 18-21 as a semi-circular tube-like shape which hollow and is open at both of its ends such that visualization by the medical professional is not unduly obstructed. In this regard, reference is made to a standard 'duck bill' speculum, incorporated herein by reference. Also provided is an insert 70 which may be slideably engaged within the sleeve 72 as shown in FIGS. 20 and 21. This embodiment may be used 'hands-free,' that is the retractor remains in place without additional securement (hand-held or mechanical) by the weight or girth of the retractor when the blade is inserted into an orifice (such as a vagina or an anus). The device would be placed within a patient with the insert 70 engaged within the sleeve 72 of the retractor. The insert 70 may then be withdrawn from the sleeve 72 providing an unobstructed line of sight through the hollow portion of the sleeve 72 by the medical professional. The blade 14 is shown as having a concave surface with LED lights (FIGS. 19 and 20), but other configurations are possible (e.g., no lights and no concave surface).

In one embodiment of the present invention, the surgical retractor 10, there is a zero degree (0°) angle between the shaft 12 and the blade 14. This may be known in the art as a thyroid/vein retractor or a one end Army-Navy retractor. In this embodiment, the L.E.D lights may be mounted on the blade 14 and/or on the distal portion of surface 16. This retractor is very useful in ENT, oral, thyroid, and breast surgery. In still another embodiment of the present invention, the surgical retractor 10 includes a blade 14 with a cross section which is convex, square, rectangular or circular. The LED lights 18 may then be mounted onto two or more separate surfaces of the blade 14 (i.e. at 2-5 surfaces for convex, square and rectangular shape, and all around the circular shape blade 14). This embodiment allows for the illumination of greater than 180 degrees in all directions vs LED lights on a single surface with an illumination of less than 180 degrees in a single direction. Furthermore, when the retractor is placed in the center of cavity, it would allow for the full illumination of the entire cavity (serve more than like a lighting mechanism than just a retractor). Additionally, a single or a plurality of CCD may be mounted on one or more surfaces of the surgical retractor 10 to permit visualization anywhere the illumination of the LED lights reaches.

1. A surgical retractor comprising:
    a shaft with an integral blade, the shaft and the blade being joined at an angle, the blade having an upper surface, one or more of LED lights being embedded within the blade and exposed at the upper surface, the blade surrounding the LED lights being opaque.

2. The surgical retractor of claim 1 wherein each of the LED lights comprises a lens and a LED, the lens being exposed at the upper surface.

3. The surgical retractor of claim 1 wherein each of the LED lights being flush with the upper surface or protruding above the upper surface.

4. The surgical retractor of claim 1 wherein the LED light emits at least 90 lumens.

5. The surgical retractor of claim 1 wherein the blade and shaft having a lower surface with an integral channel therein and a closure member covering the channel.

6. The surgical retractor of claim 1 wherein the channel houses electrical connectors for the LED lights.

7. The surgical retractor of claim 1 further comprising a power source for the LED lights in communication with the electrical connectors, and the power source being either carried on the shaft or remote from the shaft.

8. The surgical retractor of claim 1 further comprising a gripping surface on the shaft.

9. The surgical retractor of claim 1 wherein the angle between the shaft and the blade being adjustable.

10. The surgical retractor of claim 1 wherein the shaft being telescoping.

11. The surgical retractor of claim 1 further comprising a second blade facing the first mentioned blade and being moveable to and from the previous mentioned blade.

12. The surgical retractor of claim 1 wherein the upper surface being concave, flat, convex, or round.

13. The surgical retractor of claim 1 further comprising camera or cameras being mounted on the blade.

14. The surgical retractor of claim 13 wherein the camera being mounted in a second surface adjacent to the upper surface.

15. The surgical retractor of claim 13 wherein the camera or cameras can be mounted anywhere along the upper surface 16 on the blade 14 either flush with the blade 14 or on a raised surface.

16. A surgical retractor kit comprising a mounting ring, at least one surgical retractor according to claim 1, and a coupler for releasably mounting the retractor to the ring.

17. A surgical retractor comprising:
    a shaft with an integral blade, the shaft and the blade being joined at an angle, the blade having an upper surface, one or more LED lights facing up from the upper surface, a second surface at an angle to the upper surface, and a camera disposed in the second surface, wherein the camera faces down the blade and away from the upper surface.

18. The surgical retractor of claim 16 where the camera being a CCD camera.

19. The surgical retractor of claim 16 where the lights being LED lights.

20. The surgical retractor of claim 16 where the angle being 5-90°.

The present invention may be embodied in other forms without departing from the spirit and the essential attributes thereof, and, accordingly, reference should be made to the appended claims, rather than to the foregoing specification, as indicating the scope of the invention.

I claim:

1. A method of using a surgical retractor comprising the steps of:
   providing a surgical retractor comprising:
      a shaft with an integral blade, the shaft and the blade being joined at an angle, the blade having an upper surface, one or more LED lights are embedded within the blade and exposed at the upper surface, where the blade surrounding the LED lights is opaque,
      one or more electrical connectors that connect the one or more LED lights with a power source;
      one or more ridges (80) located on said shaft and located at an end opposite of the blade where each said ridge has a proximal end located toward the middle of the shaft and a distal end located on the shaft end opposite of the blade;
      the power source for the LED lights is in communication with the electrical connectors, said power source having one or more slots (41) operationally associated with the one or more ridges (80), each said slot including an open end (86) located on an end closest to a handle (82) and a barrier (88) located on the opposite end of the slot (41);
      wherein said shaft (12) is slideably engaged with the slots (41) on the power source by aligning the proximal end of each ridge(s) (80) of the shaft with the open end of each slot(s) (41) of the power source (38) and sliding the power source in a direction opposite of the blade until the proximal end of each ridge lies within each slot and engages the barrier (88) of each slot to releasably secure the shaft to the power source;
      wherein each barrier (88) prevents its corresponding ridge (80) and the shaft (12) from exiting the slot (41) while the tissue retractor is in use;
   activating the one or more LED lights;
   inserting the blade into a patient;
   pulling downward on the power source to illuminate and retract an incision or an orifice of the patient.

2. The method of claim 1 wherein the surgical retractor is constructed to be used multiple times, a single time, or a combination thereof.

3. The method of claim 1 wherein the surgical retractor is autoclaveable.

4. The method of claim 1 further comprising a pair of re-enforcing wings located at the intersection of the shaft and the blade;
   a sleeve which emanates up from the blade, wherein the sleeve is a semi-circular tube-like shape which is hollow and is open at both of its ends such that visualization by the medical professional is not unduly obstructed; and
   an insert which is removably and slideably engaged within the sleeve.

5. The method of claim 1 wherein the surgical retractor further comprises a hook emanating downward from the end of the blade opposite of the shaft.

6. The method of claim 5 wherein the surgical retractor further comprises one of more LED lights embedded within the hook.

7. The method of claim 1 wherein the surgical retractor further comprises a gripping surface on the shaft.

8. The method of claim 1 wherein the angle between the shaft and the blade is adjustable.

9. The method of claim 1 wherein the upper surface is concave, flat, convex or round.

10. The method of claim 1 wherein the surgical retractor further comprises a camera or cameras being mounted on the blade.

11. The method of claim 1 further comprising the steps of:
    providing a surgical retractor kit which includes a mounting ring and a coupler for releasably mounting each retractor to the ring;
    securing the mounting ring in a desired location;
    inserting the blade of one or more surgical retractors into the patient; and
    securing each surgical retractor to the mounting ring with a coupler.

12. A method of using a surgical retractor comprising the steps of:
    providing a surgical retractor comprising:
       a shaft with an integral blade, the shaft and the blade being joined at an angle, the blade having an upper surface, one or more LED lights facing up from the upper surface, a second surface at an angle to the upper surface, and a sleeve (72) which emanates up from the blade, wherein the sleeve (72) is a semi-circular tube-like shape which is hollow and is open at both of its ends such that visualization by the medical professional is not unduly obstructed;
       an insert (70) which is removably and slideably engaged within the sleeve (72);
       one or more electrical connectors that connect the one or more LED lights with a power source;
       one or more ridges (80) located on said shaft and located at an end opposite of the blade where each said ridge has a proximal end located toward the middle of the shaft and a distal end located on the shaft end opposite of the blade;
       the power source for the LED lights is in communication with the electrical connectors, said power source having one or more slots (41) operationally associated with the one or more ridges (80), each said slot including an open end (86) located on an end closest to a handle (82) and a barrier (88) located on the opposite end of the slot (41);
       wherein said shaft (12) is slideably engaged with the slots (41) on the power source by aligning the proximal end of each ridge(s) (80) of the shaft with the open end of each slot(s) (41) of the power source (38) and sliding the power source in a direction opposite of the blade until the proximal end of each ridge lies within each slot and engages the barrier (88) of each slot to releasably secure the shaft to the power source;
       wherein each barrier (88) prevents its corresponding ridge (80) and the shaft (12) from exiting the slot (41) while the tissue retractor is in use;
    activating the one or more LED lights;
    inserting the blade into a patient;
    positioning the blade within the patient;
    removing the insert (70) by withdrawing it from the sleeve (72) to illuminate and retract an incision or an orifice of the patient.

13. The method of claim 12 wherein the surgical retractor is constructed to be used multiple times, a single time, or a combination thereof.

14. The method of claim 12 wherein the surgical retractor is autoclaveable.

15. The method of claim 12 wherein the surgical retractor further comprises a gripping surface on the shaft.

16. The method of claim 12 wherein the angle between the shaft and the blade is adjustable.

17. The method of claim 12 wherein the surgical retractor further comprises a camera or cameras being mounted on the blade.

18. A surgical retractor comprising:
- a shaft with an integral blade, the shaft and the blade being joined at an angle, the blade having an upper surface, one or more LED lights facing up from the upper surface, a second surface at an angle to the upper surface, and a sleeve (72) which emanates up from the blade, wherein the sleeve (72) is a semi-circular tube-like shape which is hollow and is open at both of its ends such that visualization by the medical professional is not unduly obstructed and wherein the angle between the blade and the shaft is either fixed or adjustable;
- an insert (70) which is removably and slideably engaged within the sleeve (72);
- one or more electrical connectors that connect the one or more LED lights with a power source for the LED lights which is in communication with the electrical connectors, said power source being removably and slideably engaged with the shaft;
- one or more ridges (80) located on said shaft and located at an end opposite of the blade where each said ridge has a proximal end located toward the middle of the shaft and a distal end located on the shaft end opposite of the blade;
- the power source for the LED lights is in communication with the electrical connectors, said power source having one or more slots (41) operationally associated with the one or more ridges (80), each said slot including an open end (86) located on an end closest to a handle (82) and a barrier (88) located on the opposite end of the slot (41);
- wherein said shaft (12) is slideably engaged with the slots (41) on the power source by aligning the proximal end of each ridge(s) (80) of the shaft with the open end of each slot(s) (41) of the power source (38) and sliding the power source in a direction opposite of the blade until the proximal end of each ridge lies within each slot and engages the barrier (88) of each slot to releasably secure the shaft to the power source; and
- wherein each barrier (88) prevents its corresponding ridge (80) and the shaft (12) from exiting the slot (41) while the tissue retractor is in use.

19. The surgical retractor of claim 18 further comprising a camera.

* * * * *